United States Patent [19]

Zirngibl et al.

[11] 4,177,350
[45] Dec. 4, 1979

[54] IMIDAZOLE ETHYL OXYALKOXY DERIVATIVES AND THIO ANALOGUES THEREOF

[75] Inventors: Ludwig Zirngibl; Kurt Thiele, both of Zofingen, Switzerland

[73] Assignee: Siegfried Aktiengesellschaft, Zofingen, Switzerland

[21] Appl. No.: 950,825

[22] Filed: Oct. 12, 1978

[30] Foreign Application Priority Data

Oct. 13, 1977 [CH] Switzerland ............... 12528/77

[51] Int. Cl.$^2$ ............... C07D 233/60; C07D 233/94; C07D 401/12
[52] U.S. Cl. .................. 546/278; 548/341; 548/338; 424/263; 424/273 R
[58] Field of Search ............... 548/341, 338; 546/278

[56] References Cited

U.S. PATENT DOCUMENTS

| | | | |
|---|---|---|---|
| 3,658,813 | 4/1972 | Godefroi et al. | 548/341 |
| 3,682,951 | 8/1972 | Kreider | 548/341 |
| 3,839,574 | 10/1974 | Godefroi et al. | 548/341 |
| 4,055,652 | 10/1977 | Walker | 548/341 |
| 4,105,762 | 8/1978 | Miller et al. | 548/341 |

OTHER PUBLICATIONS

Hofmann Imidazole and Its Derivatives, Part I, pp. 127–135, N.Y. Interscience, 1953.
Godefroi et al., Chem. Abst., 1970, vol. 72, No. 90466v.
Gymer et al., Chem. Abst., 1977, vol. 86, No. 72645m.

*Primary Examiner*—Natalie Trousof
*Attorney, Agent, or Firm*—Werner W. Kleeman

[57] ABSTRACT

Antimycotically and antibacterially effective imidazole derivatives of the formula (1)

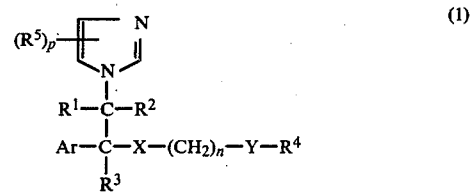

in which $R^1$, $R^2$ and $R^3$ are the same or different and are hydrogen and lower alkyl; $R^4$ is hydrogen, lower alkyl or selected from unsubstituted or substituted cycloalkyl, benzyl and phenyl groups wherein the substituents are selected from halogen, lower alkyl, lower alkoxy, lower alkylthio, phenyl, cyano, nitro and amino, or wherein $R^4$ is an unsubstituted or halosubstituted pyridyl, $R^5$ is nitro or lower alkyl in any unsubstituted position of the imidazole ring, Ar is a phenyl group optionally substituted with at least one substituent which is halogen, lower alkyl, lower alkoxy or a $C_4$–$C_8$ cycloalkyl, or wherein Ar is a benzyl group optionally substituted with a substituent of the type set forth for $R^4$, X and Y are independently selected from oxygen (—O—) or sulfur (—S—), n is an integer of from 1 to 5 inclusive and p is Zero or an integer of from 1 to 3 inclusive, and the addition salts of formula (1) compounds with pharmaceutically acceptable organic or inorganic acids; the formula (1) compounds and their addition salts as specified have a relatively low oral toxicity or/and an improved solubility and are suitable for use in human and veterinary medicine and for chemo-agricultural fungus control purposes. Suitable pharmaceutical compositions including the novel derivatives or/and their addition salts with acceptable acids as well as methods for producing such novel derivatives are disclosed.

8 Claims, No Drawings

IMIDAZOLE ETHYL OXYALKOXY DERIVATIVES AND THIO ANALOGUES THEREOF

BACKGROUND OF THE INVENTION (1) Field of the Invention

The present invention relates to novel imidazole derivatives having antimycotic and antibacterial properties and, more particularly, to certain novel imidazolyl ethyl oxyalkoxy compounds and their thio analogues as well as to the salts of addition of such compounds or their thio analogues and pharmaceutically acceptable organic or inorganic acids.

(2) Description of the Prior Art

Various imidazole derivatives and salts thereof are known to have fungicidal or antimycotic effects, e.g. the 1-($\beta$-aryl)-ethyl imidazoles disclosed in German Patent Application DE-OS No. 1,940,388 and the 1-aryl-2-(1-imidazolyl)-alkyl ethers as well as the corresponding thio ethers disclosed in German Patent Application DE-OS No. 2,619,381.

A general structure of such prior art imidazole derivatives is represented by the formula (10)

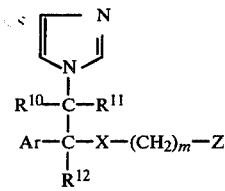

(10)

and such formula (10) compounds or their salts, respectively, are of substantial pharmacological interest in the control of mycoses, notably if the general symbols in formula (10) have the following meaning:

$R^{10}$ to $R^{12}$ are hydrogen or lower alkyl, X is oxygen or sulfur, Ar is an optionally substituted aryl group, Z is an aromatic or heteroaromatic group and m is Zero, 1 or 2. The 1-imidazolyl group may optionally carry at least one additional substituent, e.g. lower alkyl.

For chemotherapeutical purposes, notably for oral as well as rectal or vaginal administration of antimycotics in the treatment of systemic mycoses, the oral toxicity and/or the solubility of the active substance—aside from its antimycotic effectivity—are of main importance. Similar considerations apply, mutatis mutandis, to the use of fungicides in the agricultural protection of plants.

Prior art compounds of formula (10), on the other hand, tend to lack in this respect. Accordingly, it is a main object of the invention to provide for novel imidazol derivatives and salts thereof having a high antimycotic or fungicidal effectiveness combined with a substantially reduced oral toxicity.

Another object of the invention is to provide for pharmaceutical compositions containing the novel derivatives or salts thereof as an active antimycotic or fungicidal agent.

Other objects will become apparent as the specification proceeds.

SUMMARY OF THE INVENTION

In accordance with the present invention it has been found that substantial advantages in line with the above objects can be achieved without impairing the antimycotic or fungicidal effectiveness, or even with an improvement of such effectiveness, if the above prior art formula (10) is modified by an additional oxygen (—O—) or sulfur (—S—) atom between the alkylene bridge —(CH$_2$)$_m$— and group Z, that is, by replacing the prior art side chain structure (20)

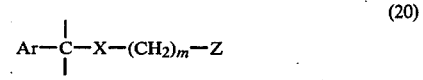

(20)

of the above identified imidazolyl structure (10) with one of the following chain structures (21)-(24) according to the invention:

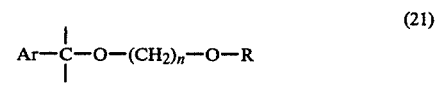

(21)

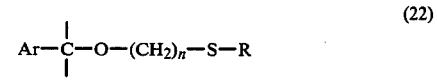

(22)

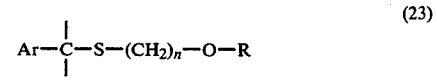

(23)

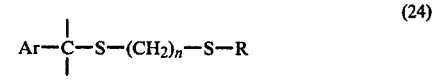

(24)

in which formulae (21)-(24) R is hydrogen, lower alkyl, an optionally substituted phenyl group or another group specified below and n is an integer of from 1 to 3 or more.

It is to be noted that group Z in some of the formula (10) compounds disclosed in German Patent Application DE-OS No. 2,619,381 may stand for a thienyl group. However, this did not permit the expectation that formula (10) compounds modified by one of the chain structures (21)-(24) would lead to comparable or even improved pharmacological properties because the cyclic sulfur atom of a heteroaromatic ring cannot be equated, in general, with the sulfur atom in an acyclic structure.

The fact that the chain structures (21)-(24) have great significance is apparent from the surprising discovery that group Z of formula (10) need not necessarily be an aromatic or heteroaromatic group—as is set forth in the above mentioned German Patent Application—but can also be replaced by an aliphatic group or even a hydrogen atom without loosing the antimycotic activity.

The novel compounds of the invention are represented by the formula (1)

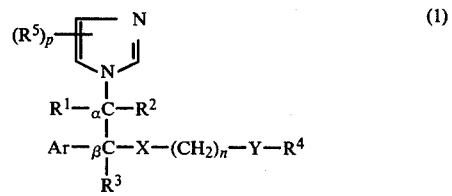

(1)

in which $R^1$, $R^2$ and $R^3$ are the same or are different and are hydrogen or lower alkyl;

$R^4$ is hydrogen, lower alkyl, $C_4$–$C_8$ cycloalkyl or a benzyl or phenyl group optionally having at least one substituent selected from halogen, lower alkyl, lower alkoxy, lower alkylthio, phenyl, cyano, nitro and amino; further $R^4$ may stand for an optionally halosubstituted pyridyl group;

$R^5$ is nitro or lower alkyl in any position of substitution of the imidazole ring;

Ar is a phenyl group optionally carrying at least one substituent selected from halogen, lower alkyl, lower alkoxy or $C_4$–$C_8$ cycloalkyl; Ar may further stand for a benzyl group optionally carrying at least one of the phenyl substituents recited above for $R^4$;

X and Y are selected independently from oxygen (—O—) and sulfur (—S—) atoms, i.e. stand for oxy and/or thio groups;

n is an integer of from 1 to 5 inclusive, and p is Zero or an integer of from 1 to 3 inclusive.

The invention includes the salts of addition formed by the formula (1) compounds and a pharmaceutically acceptable acid.

DESCRIPTION OF THE PREFERRED EMBODIMENTS

The novel compounds (1) have at least one asymmetric carbon atom (the β-carbon atom)—as do the prior art compounds (10)—and the invention generally includes both racemic mixtures of novel formula (1) compounds and the isolated stereoisomers thereof.

In the novel compounds (1) of the invention in which $R^1$ differs from $R^2$, e.g. one $R^1$ is hydrogen while the other is lower alkyl, the α-carbon atom of the formula (1) compounds will be asymmetric as well and, again, the invention includes both the racemates and the isolated stereoisomers.

Surprisingly, it was found that formula (1) compounds having an asymmetric α-carbon atom have an even more advantageous oral toxicity on mice (cf. example 25 below), i.e. have a higher $LD_{50}$ value.

Examples of suitable anorganic and organic acids that are generally considered pharmaceutically acceptable for addition salts with a pharmaceutically active base are mentioned in the above-mentioned German Patent Application.

Nitrates of formula (1) compounds are preferred acid addition salts for many purposes of the invention and nitric acid thus is a preferred acid. Other examples for suitable acids include hydrohalic acids, i.e. hydrochloric, hydrobromic and hydroiodic acid; sulfuric acid, thiocyanic acid, phosphoric acids, acetic acid, propionic acid, glycolic acid, lactic acid, pyruvic acid, oxalic acid, malonic acid, succinic acid, maleic acid, fumaric acid, malic acid, tartaric acid, citric acid, benzoic acid, cinnamic acid, mandelic acid, methane sulfonic acid, ethane sulfonic acid, hydroxy ethane sulfonic acid, p-toluene sulfonic acid, salicylic acid, p-amino salicylic acid, p-amino salicylic acid, 2-phenoxy benzoic acid and 2-acetoxybenzoic acid.

In the above definition of formula (1) the terms "lower alkyl", "lower alkoxy" and "lower alkyl thio" are intended to refer to such groups that in their alkyl moiety have from 1 to 6 carbon atoms in a straight or branched chain. Methyl is preferred for lower alkyl, lower alkoxy and lower alkyl thio; "halogen" is intended to stand for fluorine, chlorine, bromine and iodine; chlorine and bromine are generally preferred as halogen.

In a group of preferred formula (1) compounds and their salts $R^1$ is hydrogen or methyl, while both $R^2$ and $R^3$ are hydrogen and p is Zero.

Further, a preferred group of formula (1) compounds and their salts includes those where n is an integer of from 1 to 4, notably from 1 to 3. Many compounds (1) and salts thereof where n is 2 or 3 are of particular advantage.

Preferred examples of $R^4$ are methyl as lower alkyl; optionally monohalo-substituted benzyl or cyclohexyl groups, e.g. chloro-substituted benzyl; optionally mono- or disubstituted phenyl groups, wherein the substituent(s) is (are) one or two halogen atom(s), preferably chlorine and/or bromine; a lower alkyl, lower alkoxy or lower alkylthio combined, if desired, with a second substituent in the form of a halogen, or a phenyl. Preferred specific examples of $R^4$ in the form of a substituted phenyl are 2-halophenyl or 4-halophenyl (halogen is Cl or Br), 2,4-dihalophenyl or 3,4-dihalophenyl (halogen is Cl or Br), 2-methyl- or 4-methylphenyl, 2-methoxy- or 4-methoxyphenyl, 4-methylthiophenyl, 4-phenyl-phenyl, 3-methyl-4-bromophenyl, etc. Further preferred examples of $R^4$ are 4-chlorobenzyl and 5-chloropyrid-2-yl.

Preferred examples of Ar in formula (1) are phenyl substituted with one or two halogen atoms (Cl and/or Br), or with cyclohexyl or benzyl which, in turn, preferably is substituted with a halogen (Cl or Br). A preferred specific example of Ar is 2,4-dichlorophenyl.

In a further preferred group of formula (1) compounds and salts thereof, Y is oxygen when $R^4$ is hydrogen or lower alkyl. Further preferred compounds (1) and their salts are those where $R^4$ is 4-chlorophenyl and (a) X is oxygen while Y is sulfur and n is 1, or (b) both X and Y are sulfur and n is 2.

Specific examples of preferred compounds (1) and salts thereof will be given in the examples below.

Formula (1) compounds and their salts can be obtained by methods known per se, e.g. according to one of the following reactions (I) through (IV):

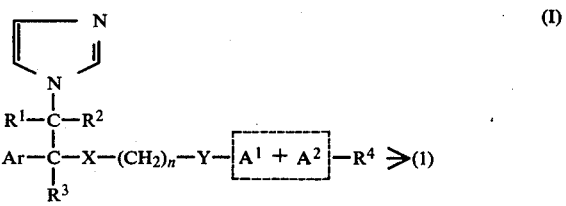

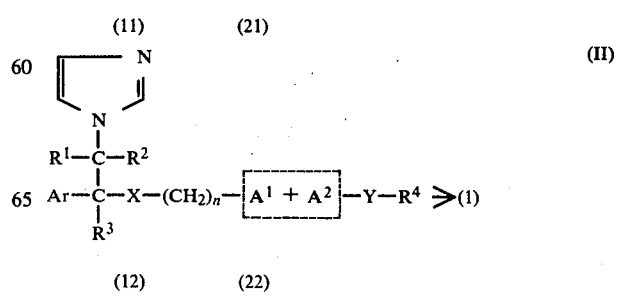

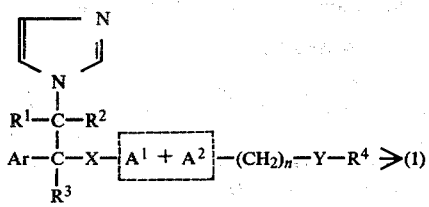

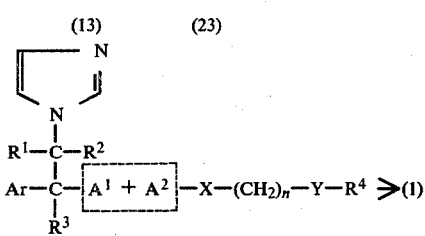

In the above reactions, $A^1$ and $A^2$ are leaving groups which under the reaction conditions are split off to form the target products of formula (1). If either $A^1$ or $A^2$ is hydrogen, it is generally preferable to convert the corresponding hydroxyl or thiol group into metal alcoholate or metal thiolate (the metal preferably being an alcali metal, e.g. sodium, potassium, etc.) prior to condensation with the second reactant wherein the other leaving group $A^2$ or $A^1$ is a halogen atom, such as notably chlorine, or a methyl sulfonyl or p-methyl benzene sulfonyl group.

Suitable condensation methods, condensation agents and reaction media for syntheses in accordance with reactions (I) through (IV) are known per se in the art, as well as methods for preparing the starting reactants. The specific reaction parameters given below in the examples are but illustrative of numerous suitable conventional means. This includes transformation of a base into a salt of addition with an acid which is a conventional method. Thus, many variations of the synthesis parameters suitable for the above reactions (I) through (IV) will be apparent to the expert and the reaction conditions set forth in the following examples are given for illustration, not limitation.

Percents are by weight; amounts are in g (grams) or ml (milliliters); temperatures are in °C. (degree Centigrade); m.p. is for melting point, b.p. is for boiling point; both being uncorrected.

EXAMPLE 1

Production of 1-β-(methoxy-methoxy-2,4-dichlorophenethyl)- imidazole nitrate of the formula

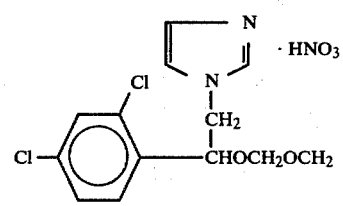

A three-necked flask provided with a thermometer, a refluxing condenser and a magnetic agitator was used; 7.71 g of α-(dichlorophenyl)-imidazole-1-ethanol (obtained according to Godefroi et al, J. Med. Chem. (1969), volume 12, page 784) were dissolved in 20 ml of hexamethyl phosphoric triamide (commercial product sold under the trade name HEXAMETAPOL) and 1.68 g of a 50% dispersion of sodium hydride in mineral oil was added. The reaction temperature rose to about 40° C. and strong foaming was observed. The mixture was stirred for 60 min at room temperature (20°–25° C.) and than heated during 60 min to 50° C. (±10° C.). The flask was cooled externally so that the temperature of the mixture was in the range of from 5° to 10° C. and a total of 2.98 g of chlorodimethyl ether was added dropwise. Then the temperature was allowed to rise to room temperature and the mixture was allowed to stand for 15 hours under such conditions.

Then the reaction mixture was poured into 450 ml of water and the resulting mass extracted in a separating funnel with three portions of 150 ml of ethyl acetate. The combined organic extracts obtained were dried over anhydrous sodium sulfate and filtered. The filtrate was evaporated under vacuum to dryness. A residue of 11.2 g of a dark and oily substance was obtained and purified by column chromatography in dichloromethane on silicagel (commercial product for dry column chromatography supplied by M. Woelm Co., Federal Republic of Germany). The eluates of the purified product—the target compound in the form of the free base—were combined and evaporated to dryness. The residue was dissolved in a mixture of ethyl acetate and diethyl ether and the target product in form of the acid addition salt (nitrate) with nitric acid was obtained by precipitation from the solution with 65% aqueous nitric acid to yield 3.6 g of the target product in the form of nearly colorless crystals. After recrystallization from a mixture of water/methanol (9:1) 2.91 g of pure target product (27% yield) were obtained as colorless crystals, m.p. 122°–123° C.

Analysis. (%) Calculated for $C_{13}H_{14}Cl_2N_2O_2 \cdot HNO_3$: 42.88 C, 4.15 H, 11.54 N; Found: 42.44 C, 4.11 H, 11.34 N.

EXAMPLES 2–20

The following compounds of formula (1) were obtained essentially in the manner of example 1 using correspondingly modified starting compounds:

(2) 1-β-(phenoxymethoxy-2,4-dichlorophenethyl)- imidazole nitrate, m.p. 138°–144° C.

(3) 1-β-(2-chlorophenoxymethoxy-2,4-dichlorophene- thyl)-imidazole nitrate, m.p. 152°–153° C.

(4) 1-β-(4-chlorophenoxymethoxy-2,4-dichlorophene- thyl)-imidazole nitrate, m.p. 144°–145° C.

(5) 1-β-(2,4-dichlorophenoxymethoxy-2,4-dichloro- phenethyl)-imidazole nitrate, m.p. 154°–157° C.

(6) 1-β-(4-methylphenoxymethoxy-2,4-dichlorophene- thyl)-imidazole nitrate, m.p. 158°–159° C.

(7) 1-β-(4-methoxyphenoxymethoxy-2,4-dichloro- phenethyl)-imidazole nitrate, m.p. 130°–132° C.

(8) 1-β-(4-methylthiophenoxymethoxy-2,4-dichloro- phenethyl)-imidazole nitrate, m.p. 142°–143° C.

(9) 1-β-(phenylphenoxymethoxy-2,4-dichlorophene- thyl)-imidazole nitrate, m.p. 172°–173° C.

(10) 1-β-(methylthiomethoxy-2,4-dichlorophenethyl)- imidazole nitrate, m.p. 144°–145° C.

(11) 1-β-(phenylthiomethoxy-2,4-dichlorophenethyl)- imidazole nitrate, m.p. 142°–143° C.

(12) 1-β-(4-bromophenylthiomethoxy-2,4-dichloro- phenethyl)-imidazole nitrate, m.p. 155°–157° C.

(13) 1-β-(4-chlorophenylthiomethoxy-2,4-dichlorophenethyl)-imidazole nitrate, m.p. 140°–142° C.
(14) 1-β-(4-methylphenylthiomethoxy-2,4-dichlorophenethyl)-imidazole nitrate, m.p. 144°–145° C.
(15) 1-β-(3,4-dichlorophenylthiomethoxy-2,4-dichlorophenethyl)-imidazole nitrate, m.p. 112°–113° C.
(16) 1-β-(4-bromo-3-methylphenylthiomethoxy-2,4-dichlorophenethyl)-imidazole nitrate, m.p. 127°–129° C.
(17) 1-{β-[2-(p-chlorophenoxyethoxy)-ethoxy-2,4-dichlorophenethyl]}-imidazole nitrate, m.p. 120°–104° C.
(18) 1-β-(2,4-dichlorophenethyl-β'-hydroxyethylthio)-imidazole nitrate, m.p. 90°–92° C.
(19) 1-[β-methylthiomethoxy-4-(4'-chlorobenzyl)-phenethyl]-imidazole nitrate, m.p. 145°–147° C.
(20) 1-β-(3-phenoxypropyloxy-2,4-dichlorophenethyl)-imidazole methane sulfonate, m.p. 90°–92° C.

EXAMPLE 21

Production of 1-β-(4-chlorophenylthioethylthio-2,4-dichlorophenethyl)-imidazole of the formula

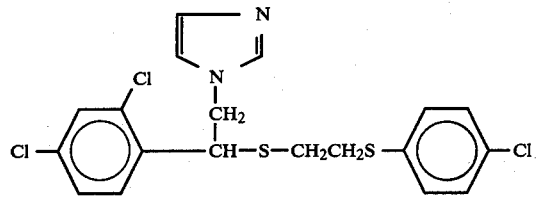

The synthesis route of reaction IV above was followed with $A^1$=Cl and $A^2$=H. The compound of the formula (24) of reaction IV thus is 2-(4-chlorophenylthio)-ethyl mercaptane that was obtained as follows: a mixture of 14.5 g of p-chlorophenol, 6.61 g of ethylene sulfide, 1.25 ml of triethyl amine and 50 ml of mineral spirit (boiling range of 35° to 70° C.) was refluxed for 7 hours on an oil bath at about 50° C. Then the mixture was allowed to cool and to stand over night. Thereafter, the reaction mixture was evaporated under vacuum to yield 20.36 g of an oily residue which, in turn, was distilled under vacuum to yield 14.3 g of 2-(4-chlorophenylthio)-ethyl mercaptane (yield is 70%) boiling at 110°–112° C./0.5 mm Hg and having a refractive index $n_D^{20}$ of 1.6238.

Analysis. (%) Calculated for $C_8H_9ClS_2$: 46.93 C, 4.43 H; Found: 47.20 C, 4.56 H.

A mixture of 10.23 g of the mercaptane so obtained and 19.00 g of 1-(2,4-dichlorophenyl)-2-(1-imidazolyl)-ethyl chloride in the form of its hydrochloride-semizincchloride salt, 16.6 g of pulverized anhydrous potassium carbonate and 300 ml of methyl-isobutyl ketone was refluxed during a period of 12 hours. The reaction mixture was filtered while still hot and the filtrate evaporated under vacuum. A residue in an amount of 24.5 g and in the form of a light-brown oil was obtained and purified by chromatography with methylene chloride on silicagel (by Woelm as in example 1). The fractions containing the pure product were combined and evaporated to dryness. The residue in an amount of 12.3 g (55% yield) is the target compound of this example in the form of a lightly colored oil (free base).

Analysis. (%) Calculated for $C_{19}H_{17}Cl_3N_2S_2$: 51.41 C, 3.86 H, 6.31 N; Found: 51.27 C, 3.90 H, 6.18 N.

EXAMPLES 22–28

The following formula (1) compounds were obtained by the method of example 1 using correspondingly modified reactants:
(22) 1-[β-(cyclohexylthiomethoxy-2,4-dichlorophenethyl)]-imidazole nitrate, m.p. 144°–145° C.
(23) 1-β-(p-chlorobenzylthiomethoxy-2,4-dichlorophenethyl)-imidazole nitrate, m.p. 139°–140° C.
(24) 1-β-(2-methoxyphenoxymethyloxy-2,4-dichlorophenethyl)-imidazole nitrate, m.p. 125°–126° C.
(25) 1-[β-(p-chlorophenylthiomethoxy)-2,4-dichlorophenethyl-α-methyl]-imidazole nitrate, m.p. 115°–126° C.
(26) 1-β[(5'-chloropyridyl-2'-thiomethoxy)-2,4-dichlorophenethyl)]-imidazole nitrate, m.p. 159°–161° C.
(27) 1-β-(phenoxyethoxy-2,4-dichlorophenethyl)-imidazole nitrate, m.p. 111°–112° C.
(28) 1-[β-(p-chlorophenoxyethoxy)-2,4-dichlorophenethyl)]-imidazole nitrate, m.p. 129.5° to 132.5° C.

EXAMPLE 29

In the general manner described in example 21 the starting reactant 2-(5'-chloropyridyl-2'-thio)-ethyl mercaptane was produced from ethylene sulfide and 5-chloropyridine-2-mercaptane. The starting reactant was then reacted in the general manner described in example 21 to yield the target compound of the present example 29, the 1-{β-[(5'-chloropyridyl-2'-thio-2-ethylthio)-2,4-dichlorophenethyl]}-imidazole. This compound (free base) was obtained in the form of a syrup-type liquid.

Analysis. (%) Calculated for $C_{18}H_{16}Cl_3N_3S_2$: 48.60 C, 3.63 H, 9.45 N, 14.42 S, 23.91 Cl; Found: 48.76 C, 3.75 H, 9.10 N, 14.20 S, 24.30 Cl.

EXAMPLES 30–31

The following compounds were produced in the general manner described in example 1:
(30) 1-{β-[3-(p-chlorophenoxy)-propoxy-2,4-dichlorophenethyl]}-imidazole nitrate, m.p. 118°–119° C.
(31) 1-{β-[3-(p-chlorophenylthio)-propoxy]-2,4-dichlorophenethyl}-imidazole nitrate, m.p. 108°–110° C.

EXAMPLE 32

3-Phenoxypropylbromide was reacted in 95% ethanol under reflux with thio-urea during a period of 4 hours to yield the starting reactant 3-phenoxypropylmercaptane, b.p. 121°–123° C./9 mbar. This reactant was used in the process of example 21 to yield the target product of present example 32, i.e. the 1-[β-(phenoxypropylthio)-2,4-dichlorophenethyl]-imidazole. This compound (free base) was obtained as a viscous oil and purified by chromatography on a silicagel column with $CH_2Cl_2/CHCl_3$.

Analysis. (%) Calculated for $C_{20}H_{20}Cl_2N_2OS$: 58.97 C, 4.95 H, 6.88 N, 7.87 S, 17.41 Cl; Found: 59.01 C, 5.13 H, 6.52 N, 7.50 S, 17.63 Cl.

EXAMPLE 33

The starting reactant of this example, i.e. 3-(4-chlorophenoxy)-propylmercaptane, b.p. 83°–93° C./0.006 mbar, was obtained according to the general method described in example 32 and was then reacted in the general manner of example 21 to yield the target product of present example 33, i.e. 1-{β-[3-(p-chlorophenoxy)-propylthio-2,4-dichlorophenethyl]}-imidazole, that was purified in accordance with example 32 and gave the following indentification result:

Analysis. (%) Calculated for $C_{20}H_{19}Cl_3N_2OS$: 54.37 C, 4.33 H, 6.34 N; Found: 54.44 C, 4.73 H, 6.02 N.

EXAMPLE 34

In a manner similar to that of example 32 3-(4-chlorophenylthio)-propylchloride, b.p. 116°–120° C./0.4 mbar, was used to produce 3-(4-chlorophenylthio)-propylmercaptane, b.p. 120°–125° C./0.2 mbar, and the latter compound was reacted in the general manner of example 21 to yield the target product of present example 34, i.e. 1-{β-[3-(p-chlorophenylthiopropylthio)]-2,4-dichlorophenethyl}-imidazole nitrate, m.p. 79°–83° C. Product purification was as described in example 32.

EXAMPLES 35–36

According to the general procedure of example 1 the 4-(4-chlorophenoxy)-butylbromide, b.p. 114°–120° C./0.6 mbar, was used to produce the target product of example 35, i.e. the 1-{β-[4-(p-chlorophenoxy)-butoxy]-2,4-dichlorophenethyl}-imidazole nitrate, m.p. 110°–113° C.

The starting reactant used to produce the target compound of example 35 was obtained by heating a mixture of 1,4-dibromobutane, 4-chlorophenol and $K_2CO_3$ in dimethyl formamide during a period of 6 hours.

In an analogous manner, the 4-(4-chlorophenylthio)-butyl bromide, b.p. 132°–135° C./0.05 mbar, was used as starting reactant to produce the target product of example 36, i.e. the 1-{β-[4-(p-chlorophenylthio)-butoxy]-2,4-dichlorophenethyl}-imidazole nitrate, m.p. 105°–108° C.

The formula (1) compounds and their addition salts with acids obtained according to examples 1–36 were tested to determine their minimum inhibitory concentrations (MIC) in micrograms per milliliter (μg/ml) for various bacteria and microfungi according to the conventional gradient plate method at gradients of from Zero to 100 μg/ml and in the form of solutions in 10% aqueous dimethyl formamide. Test evaluation was made three days after inoculation. The results of these tests are summarized in the following Table I together with the oral toxicity values ($LD_{50}$ per os; mice, values in mg per kg of body weight) determined in the conventional manner. For comparative purposes, the corresponding values are given for ECONAZOLE (toxicity value as reported by Thienpont et al, Arzneimittelforschung, 1975, volume 25, page 224), a prior art compound of a formula (10) nitrate salt, wherein $R^{10}$, $R^{11}$ and $R^{12}$ are hydrogen, Ar is 2,4-dichlorophenyl, X is oxygen, m is 1 and Z is 4-chlorophenyl.

TABLE I

| Example No. | Toxicity $LD_{50}$ per os (mg/kg) (mice) | Minimum Inhibitory Concentration (μg/ml) | | | |
|---|---|---|---|---|---|
| | | Bacteria | | Fungi | |
| | | St[A] | Str[B] | Tri[C] | Asp[D] |
| 1 | 540 | | <10 | <10 | |
| 2 | >3000 | 10 | 25 | <10 | <10 |
| 3 | >3000 | <10 | 15 | <10 | <10 |
| 4 | ca. 2750 | <10 | <10 | <10 | <10 |
| 5 | >>3000 | <10 | <10 | <10 | <10 |
| 6 | >3000 | <10 | 15 | <10 | <10 |
| 7 | 2600 | 10 | 30 | <10 | <10 |
| 8 | ca. 2100 | 10 | | <10 | <10 |
| 9 | ca. 3500 | | | | |
| 10 | ca. 950 | 20 | 30 | <10 | <10 |
| 11 | >3000 | <10 | 20 | <10 | <10 |
| 12 | 12500 | <10 | 10 | <10 | <10 |
| 13 | 3850 | 10 | 10 | <10 | <10 |
| 14 | >>3000 | <10 | <10 | <10 | <10 |
| 15 | ~7500 | <10 | <10 | <10 | 25r[E] |
| 16 | >>3000 | <10 | 10 | <10 | <10 |
| 17 | 2500 | <10 | 10 | <10 | 10 |
| 18 | 1300 | 50 | 40 | 30 | |
| 19 | 970 | 10 | 25 | <10 | 10 |
| 20 | ~2400 | <10 | <10 | <10 | <10 |
| 21 | >3000 | <10 | | <10 | <10 |
| 22 | >3000 | <10 | <10 | <10 | <10 |
| 23 | >>2000 | <10 | | <10 | <10 |
| 24 | ~1350 | r[E] | | <10 | <10 |
| 25 | >>10000 | <10 | <10 | <10 | r[E] |
| 26 | ~2700 | 10 | 20 | <10 | <10 |
| 27 | ~800 | 20r[E] | 30 | <10 | <10 |
| 28 | >>3000 | <10 | 10 | <10 | <10 |
| 29 | >>2000 | <10 | | <10 | <10 |
| 30 | >4000 | <10 | <10 | <10 | <10 |
| 31 | 4300 | <10 | <10 | <10 | <10 |
| 32 | >>2000 | <10 | r[E] | <10 | <10 |
| 33 | >1000 | <10 | 10 | <10 | 25 |
| 34 | >>3000 | 10 | r[E] | <10 | r[E] |
| 35 | >>4000 | 10 | r[E] | <10 | <10 |
| 36 | >>3000 | <10 | r[E] | <10 | 35 |
| ECONAZOLE (Comparison) | 462.7 | <10 | <10 | <10 | <10 |

The abbreviations used in Table I have the following meanings:
[A]St = *Staphylococcus aureus haemolyticus*
[B]Str = *Streptococcus faecalis*
[C]Tri = *Trichophyton mentagrophytes*
[D]Asp = *Aspergillus niger*
[E]r = partial resistancy observed In view of the results reported above a group of preferred formula (1) compounds and salts according to the invention includes the target products of examples 2, 4, 7, 8, 11, 20, 23, 26 and 35. Another even more preferred group of formula (1) compounds and salts according to the invention includes the target compounds of examples 5, 6, 12, 13, 14, 15, 25, 28, 30, 31 and 32.

EXAMPLES 37–39

The following formula (1) compounds were produced according to the methods described above:
(37) 1-{β-[5-p-chlorophenylthio)-pentoxy]-2,4-dichlorophenethyl}-imidazole as the methane sulfonate salt, m.p. 130°–130.5° C.
(38) 1-{β-[5-(p-chlorophenoxy)-pentoxy]-2,4-dichlorophenethyl}-imidazole as the methane sulfonate salt, m.p. 138°–139° C.
(39) 1-{β-[5-(p-chlorophenoxy)-pentylthio]-2,4-dichlorophenethyl}-imidazole as the nitrate salt, m.p. 88°–89° C.

The MIC values of the formula (1) compounds of examples 37 to 39 indicated that their effeciveness against bacteria and fungi was somewhat lower if compared with formula (1) compounds according to the invention having a shorter —$(CH_2)_n$— chain (i.e. with n being smaller than 5); however, if compared with ECONAZOLE, the compounds of examples 37–39 have substantially decreased oral toxicity.

The novel inventive formula (1) compounds and their salts can be used per se, i.e. without additives, as antimycotics or fungicides. Preferably, however, they are applied in admixture with (this includes solutions) conventional carriers, diluents, adjuvants and the like known to be pharmaceutically acceptable. Such carriers can be liquids, e.g. water or isotonic saline solution, pastes, e.g. unguent bases, such as polyethylene oxides, or solids, such as starch or talcum. Suitable selection of such carriers and the methods of combining them with therapeutically effective substances—e.g. by blending, mixing, emulsifying or dissolving—are known per se as well for prior art antimycotics (cf. German Patent Application No. 2,619,381 mentioned above) and can be used to prepare compositions according to the present invention.

The novel formula (1) compounds and their salts according to the invention can be used as the only active ingredient of such compositions or in mixture with other therapeutically active components. Preferred compositions are those for oral or topical administration in human or veterinary medicine. Injectable solutions for the novel compounds can be prepared and used as well.

The concentration of the active formula (1) ingredient or its salt in a composition according to the invention may be as low as a fraction of a percent, e.g. 0.1%, generally at least about 1%, and as high as 90% or even more. For many purposes, a concentration of the active ingredient in the range of from 1% to about 50% is suitable.

Thus, an effective amount of the active ingredient in a composition according to the invention may be in the broad range of from 0.1 to 90%.

Some illustrative but not limitative examples of such compositions are given below (parts are by weight):

(A) 70 parts of formula (1) ingredient was mixed with 3 parts of corn starch and 22 parts of lactose. The mixture was granulated. An additional amount of 3 parts of corn starch and 1 parts of magnesium stearate were added. The mixture was granulated again and filled into capsules for oral administration.

(B) 2 parts of formula (1) active ingredient were blended with 10 parts of low molecular polyethylene glycol and the blend was admixed with 88 parts of an unguent base to form a cream for topical administration.

(C) A blend of 2 parts of formula (1) active ingredient and 8 parts of corn starch was premilled. Then, 90 parts of talcum powder were added and the resulting mixture was milled to dusting-powder fineness to form a dusting powder for topical administration.

(D) 2 parts of formula (1) active ingredient was mixed with 98 parts of a suppository base, heated above its temperature of liquification, to form suppositories for rectal or vaginal application.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A compound of the formula (1)

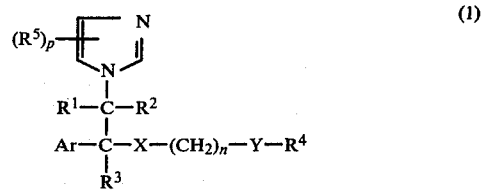

in which $R^1$, $R^2$ and $R^3$ are individually selected from the group consisting of hydrogen and lower alkyl; $R^4$ is selected from the group consisting of hydrogen; lower alkyl; $C_4$-$C_8$ cycloalkyl or a benzyl or phenyl group having at least one substituent selected from the group consisting of halogen, lower alkyl, lower alkoxy, lower alkylthio, phenyl, cyano, nitro and amino; and unsubstituted and halosubstituted pyridyl; $R^5$ is selected from the group consisting of nitro and lower alkyl; Ar is selected from the group consisting of unsubstituted and substituted phenyl having at least one substituent selected from the group consisting of halogen, lower alkyl and lower alkoxy; and unsubstituted and substituted benzyl having at least one substituent selected from the group consisting of substituents specified for $R^4$; X and Y are individually selected from the group consisting of oxygen and sulfur atoms; n is an integer of from 1 to 5 inclusive and p is selected from the group consisting of Zero and integers of from 1 to 3 inclusive provided that p does not exceed 1 where $R^5$ is nitro; and addition salts of said formula (1) compounds with pharmaceutically acceptable acids.

2. The compound of claim 1 wherein $R^1$ is selected from the group consisting of hydrogen and methyl; $R^2$ and $R^3$ each are hydrogen; and p is Zero, and addition salts of said compound with a pharmaceutically acceptable acid.

3. The compound of claim 1 wherein $R^4$ is selected from the group consisting of hydrogen; lower alkyl; unsubstituted and halogen-substituted benzyl, cyclohexyl and pyridyl; unsubstituted and substituted phenyl having from 1 to 2 substituents selected from the group consisting of halogen, lower alkyl, lower alkoxy, lower alkylthio, and phenyl; and addition salts of said compound with a pharmaceutically acceptable acid.

4. The compound of claim 3 wherein $R^4$ is selected from the group consisting of methyl, phenyl, 2-chlorophenyl, 4-chlorophenyl, 4-bromophenyl, 2,4-dichlorophenyl, 3,4-dichlorophenyl, 4-methylphenyl, 2-methoxyphenyl, 4-methoxyphenyl, 4-methylthiophenyl, 4-phenyl-phenyl, 3-methyl-4-bromophenyl, cyclohexyl, 4-chlorobenzyl and 5-chloropyrid-2-yl; and addition salts of said compound with a pharmaceutically acceptable acid.

5. The compound of claim 1 wherein n is selected from integers of from 1 to 3 inclusive, and addition salts of said compound with a pharmaceutically acceptable acid.

6. The compound of claim 1 wherein Ar is selected from the group consisting of phenyl, monohalo-substituted phenyl, dihalo-substituted phenyl, benzyl, halo-substituted benzyl; and addition salts of said compound with a pharmaceutically acceptable acid.

7. The compound of claim 6 wherein Ar is dihalo-substituted phenyl.

8. The compound of claim 6 wherein Ar is 2,4-dichlorophenyl.

* * * * *